(12) United States Patent
Mullin et al.

(10) Patent No.: US 9,723,986 B1
(45) Date of Patent: Aug. 8, 2017

(54) PHYSIOLOGICAL PARAMETER MEASURING SYSTEM

(71) Applicant: Welch Allyn, Inc., Skaneateles Falls, NY (US)

(72) Inventors: Matthew D. Mullin, Memphis, NY (US); David E. Quinn, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 15/009,496

(22) Filed: Jan. 28, 2016

(51) Int. Cl.
*A61B 5/00* (2006.01)
*A61B 5/01* (2006.01)
*A61B 5/0205* (2006.01)

(52) U.S. Cl.
CPC ............ *A61B 5/002* (2013.01); *A61B 5/0008* (2013.01); *A61B 5/01* (2013.01); *A61B 5/02055* (2013.01); *A61B 5/6833* (2013.01); *A61B 5/742* (2013.01); *A61B 2562/0271* (2013.01)

(58) Field of Classification Search
CPC ......... A61B 5/002; A61B 5/0008; A61B 5/01; A61B 5/02055; A61B 5/6833; A61B 5/742
See application file for complete search history.

(56) References Cited

U.S. PATENT DOCUMENTS

| | | | |
|---|---|---|---|
| 4,878,184 A | 10/1989 | Okada et al. | |
| 4,986,669 A | 1/1991 | Yamaguchi | |
| 7,549,792 B2 | 6/2009 | Bisch et al. | |
| 8,449,476 B2 | 5/2013 | Waldhoff et al. | |
| 8,930,147 B2 | 1/2015 | Pollack et al. | |
| 2006/0006987 A1* | 1/2006 | Hashimoto | G06K 7/0008 340/10.51 |
| 2008/0161657 A1* | 7/2008 | Bullens | A61B 5/0031 600/301 |
| 2015/0272494 A1* | 10/2015 | Fuerst | A61B 5/4094 600/301 |

FOREIGN PATENT DOCUMENTS

| | | |
|---|---|---|
| CN | 102370464 A | 3/2012 |
| CN | 203736174 U | 7/2014 |
| CN | 204292295 U | 4/2015 |
| EP | 1667082 A1 | 6/2006 |
| JP | 2008/538965 A | 11/2008 |

(Continued)

OTHER PUBLICATIONS

Stackexchange, "Fast-Stabilising Skin Temperature Sensor", Retrieved on: Jul. 29, 2015, available at: http://electronics.stackexchange.com/questions/115976/fast-stabilising-skin-temperature-sensor.

(Continued)

*Primary Examiner* — Leon Flores
(74) *Attorney, Agent, or Firm* — Merchant & Gould P.C.

(57) ABSTRACT

A physiological parameter measuring system includes a parameter sensing device attachable to a body of the subject. The sensing device detects at least one physiological parameter when activated, and a reading device monitors a temperature variation over time and determines whether the parameter has been so stabilized as to be reliably detected. A stability indication flag can be stored in the system so that subsequent monitoring of the parameter is instantly performed.

18 Claims, 11 Drawing Sheets

(56) References Cited

FOREIGN PATENT DOCUMENTS

JP          2013/000131 A      1/2013
KR       2014/0016460 A       2/2014

OTHER PUBLICATIONS

Rene Rossi and Marc Correvon, "Predicting body Core Temperature using Non-Invasive Sensors", Sep. 30, 2011.
Pultronics, "Wireless Temperature Sensor", Aug. 27, 2010.
Vaz; A. Ubarretxena; Ibon Zalbide; D. Pardo; H. Solar; and A. Garcia-Alonso, "Full Passive UHF Tag With a Temperature Sensor Suitable for Human Body Temperature Monitoring", Article in Circuits and Systems II: Express Briefs, IEEE Transactions Mar. 2010.

* cited by examiner

US 9,723,986 B1

PHYSIOLOGICAL PARAMETER MEASURING SYSTEM

BACKGROUND

The measurement of a body temperature using a thermometer device is not typically able to be performed instantly and requires an extended period of time up to at least a few minutes. Such measurement time delay can be caused by the heat capacity of a sensing element of the thermometer device and the fact that applying the thermometer device to the patient tissues or skin draws down the temperature of the tissues or skin in the immediate region of the thermometer device.

SUMMARY

In general terms, this disclosure is directed to a physiological parameter measuring system. In one possible configuration and by non-limiting example, the system is configured to determine the stability of a parameter before the parameter is detected, and a stability indication is used for instant measurement of the parameter. Various aspects are described in this disclosure, which include, but are not limited to, the following aspects.

One aspect is a system for monitoring a physiological parameter of a subject. The system includes a parameter sensing device attachable to a body of the subject, the parameter sensing device configured to detect at least one physiological parameter when attached to the body of the subject and activated, and a reading device configured to: transmit a trigger signal to the parameter sensing device to activate the parameter sensing device; obtain a first physiological parameter at a first time using the parameter sensing device; obtain a second physiological parameter at a second time using the parameter sensing device, the second time being later than the first time; calculate a parameter difference between the first physiological parameter and the second physiological parameter; compare the parameter difference with a threshold; and if the parameter difference is less than the threshold, store a stability indication flag in the parameter sensing device, the stability indication flag adapted for indicating that the physiological parameter has stabilized over time.

Another aspect is a method of obtaining a physiological parameter of a subject. The method includes obtaining a first physiological parameter at a first time using a parameter sensing device, the parameter sensing device attached to a body of the subject; obtaining a second physiological parameter at a second time using the parameter sensing device, the second time being later than the first time; calculating a parameter difference between the first physiological parameter and the second physiological parameter; comparing the parameter difference with a threshold; and if the parameter difference is less than the threshold, storing a stability indication flag in the parameter sensing device, the stability indication flag adapted for indicating that physiological parameter has stabilized over time.

Yet another aspect is an apparatus for communicating with a temperature sensing device and obtaining a temperature of a subject from the temperature sensing device. The apparatus includes: a processing device configured to control operation of the apparatus; a display screen; and a computer readable data storage device storing software instructions that, when executed by the processing device, cause the apparatus to: transmit a trigger signal to the temperature sensing device to activate the temperature sensing device, the temperature sensing device attached to a body of the subject; obtain a first temperature at a first time using the temperature sensing device; obtain a second temperature at a second time using the temperature sensing device, the second time being later than the first time; calculate a temperature difference between the first temperature and the second temperature; compare the temperature difference with a threshold; if the temperature difference is less than the threshold, store a stability indication flag in the temperature sensing device, the stability indication flag adapted for indicating that the temperature has stabilized over time; predict a stabilized temperature before the temperature is stabilized over time; display the stabilized temperature as a detected temperature on the display screen; and deactivate the temperature sensing device.

DETAILED DESCRIPTION

Figure 1:
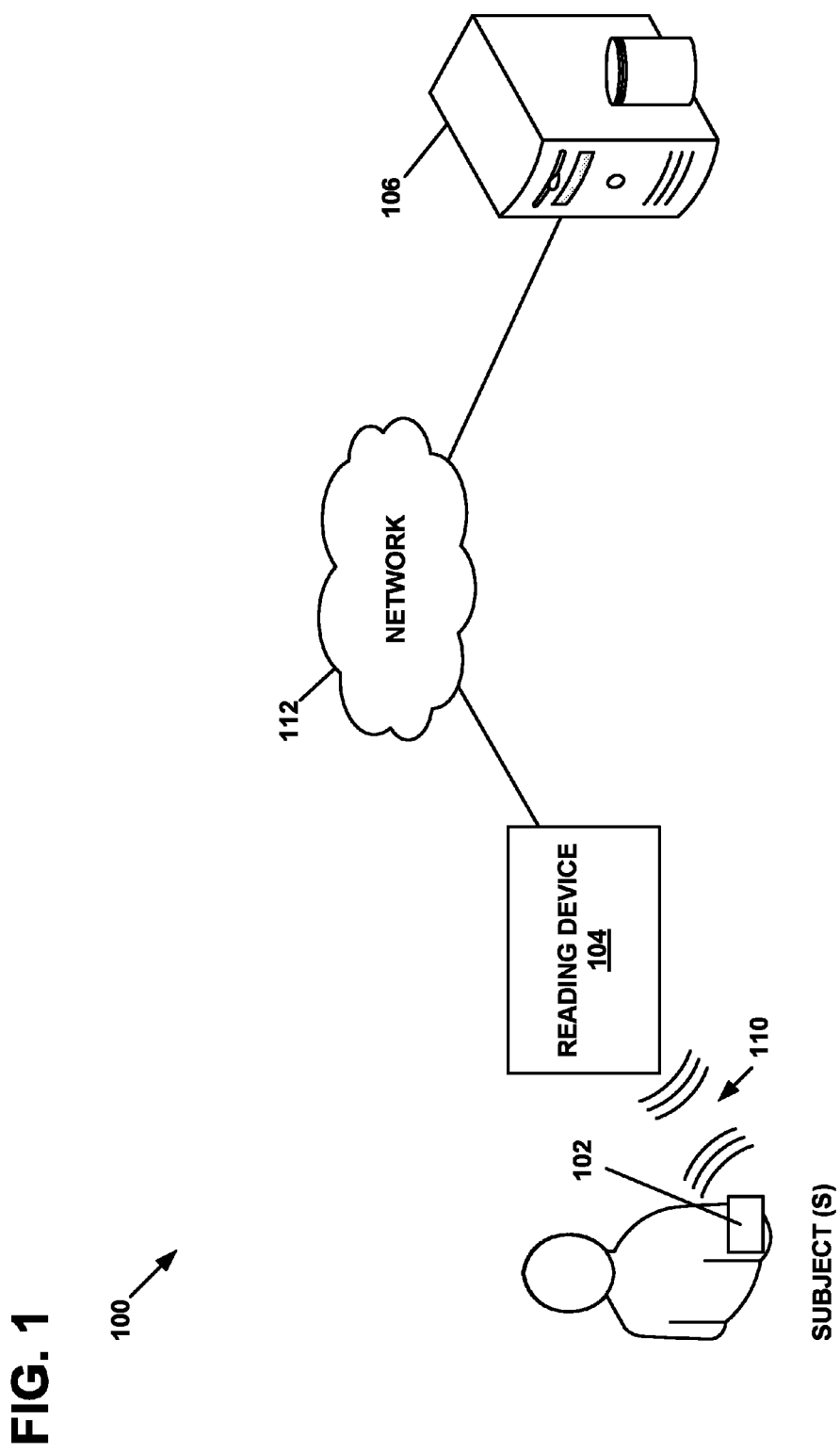
FIG. 1 schematically illustrates a system for wirelessly sensing one or more physiological parameters of a subject in accordance with an exemplary embodiment of the present disclosure.

Various embodiments will be described in detail with reference to the drawings, wherein like reference numerals represent like parts and assemblies throughout the several views.

In general, a system in accordance with an exemplary embodiment of the present disclosure provides a quick response in monitoring a physiological parameter of a subject, thereby allowing instant measurements of the parameter associated with the subject. In some examples, the system of the present disclosure includes a body-worn sensing patch (e.g., a temperature monitoring patch) that is activated to detect a physiological parameter (e.g., a body temperature) of the subject and communicate with a reading device via a wireless communication link. In some examples, the sensing patch is designed for a single use. When the sensing device is first attached to the subject's body or reattached to the body after detached, there exists a thermal unbalance between the subject's body and the sensing device that has just been engaged with the body. Until the sensing device reaches thermal equilibrium with the subject's body to which the sensing device is attached, the reading device monitors the parameter variation over time and determines whether the parameter has been so stabilized as to be reliably detected. Once it is determined that the parameter is stable, a stability indication flag is stored in the system so that any subsequent monitoring of the parameter is instantly performed without monitoring a change of the parameter over time. Until the stability indication flag is created and stored, the reading device can predict the parameter (e.g., the body temperature) based on the parameter variation over time, thereby saving time in obtaining the parameter.

FIG. 1 schematically illustrates an example system 100 for wirelessly sensing one or more physiological parameters of a subject S. The system 100 can include a physiological parameter sensing device 102, a reading device 104, and a data management system 106. The physiological parameter sensing device 102 can communicate with the reading device 104 via a wireless communication link 110. The reading device 104 can communicate with the data management system 106 via a data communication network 112.

The physiological parameter sensing device 102 is worn or carried by the subject S. In some examples, the sensing device 102 includes a physiological parameter sensing patch as described below. In this document, therefore, the sensing device 102 is also referred to as a physiological parameter sensing patch 102.

In some examples, the sensing device 102 is removably attached to a portion of the subject's body or the subject's skin. The sensing device 102 can be worn on different locations of the subject body, such as the forehead, torso, neck, arm, leg, or other on-body locations, for different measurements. In other examples, the sensing device 102 is implanted to the subject's body. The sensing device 102 can be attached or implanted to the subject S by a healthcare practitioner when the healthcare practitioner sees the subject S. In other examples, the subject S can wear or attach the sensing device 102 on his or her own.

The sensing device 102 operates to detect one or more physiological parameters of the subject S. The subject S can also be referred to herein as a patient or person. The sensing device 102 is configured to detect one or more physiological parameters. In some examples, the sensing device 102 includes one sensor unit 132 (FIG. 3) to measure the same type of physiological parameters. In other examples, the sensing device 102 includes a plurality of sensor units 132 of different types capable of detecting different kinds of physiological parameters. The sensing patch 102 transmits signals to the reading device 104 via the wireless communication link 110.

Physiological parameters can include vital signs, physiological measurements, and biological measurements, which can be detected from various portions of the subject's body. For example, physiological parameters include measurements of the body's basic functions, which are useful in detecting or monitoring medical problems. Examples of physiological parameters include body temperature, pulse rate (i.e., heart rate), respiration rate (i.e., breathing rate), blood pressure, blood gas, and SpO2. Body temperature can be taken in various manners, such as orally, rectally, by ear, or by skin. The pulse rate is a measurement of the heart rate, or the number of times the heart beats per minute. The pulse rate can also indicate a heart rhythm and the strength of the pulse. The pulse can be taken on different body portions where the arteries are located, such as on the side of the neck, on the side of the elbow, or at the wrist. The respiration rate is the number of breaths a person takes per minute and is used to note whether the person has any difficulty breathing. Blood pressure is the force of the pushing against the artery walls. There may be other vital signs, such as pain, Glasgow coma scale, pulse oximetry, blood glucose level, end-tidal $CO_2$, functional status, shortness of breath, and gait speed.

In the present disclosure, the sensing device 102 is primarily described to be capable of measuring body temperature of the subject S. In other embodiments, however, the sensing device 102 can be configured to measure different physiological parameters, such as blood gas, SpO2, blood pressure, heart rate, and any other parameters, in addition to or in lieu of body temperature.

In some examples, the sensing patch 102 is configured as a passive device, which does not include an independent power source, such as a battery, to supply power to the components of the sensing patch 102. In this configuration, the sensing patch 102 can be activated by the reading device 104 when the reading device 104 comes close to the sensing patch 102 within a predetermined activation or read range. In other examples, the sensing patch 102 is configured as an active device, which includes its own power supply. An example of the sensing device 102 is described and illustrated in more detail with reference to FIGS. 3 and 4.

With continued reference to FIG. 1, the reading device 104 operates to communicate with the sensing device 102 attached to the subject S. The reading device 104 can receive signals from the sensing patch 102 via the wireless communication link 110. In some examples, the reading device 104 is operable to present the data transmitted from the sensing patch 102 thereon. For example, the reading device 104 includes a display screen and operates to present the transmitted data on the screen in a visible format. The reading device 104 can output the data in an audible format, and/or provide an alert in visible and/or audible manners. The reading device 104 can also be in communication with the data management system 106 via the network 112.

The reading device 104 can be used by a guardian and/or a healthcare practitioner to monitor the measurement of the sensing device 102. The guardian is a person or a group of people who is interested in the health conditions of the subject S. Examples of the guardian include a parent of the subject S, a family member of the subject S, a caregiver of the subject S, a primary physician of the subject S, and any other interested parties. The healthcare practitioner is a person who provides healthcare service to the subject S. Examples of healthcare practitioners P include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services. The healthcare practitioner can be an institution, company, business, and/or entity. In other examples, the reading device 104 can be operated by the subject S him or herself.

The reading device 104 can be of various types. In some examples, the reading device 104 is a computing device dedicated for particular sensing devices 102. In other examples, other consumer level computing devices can be used for the reading device 104. Such computing devices can include a mobile computing device, such as a smartphone, (e.g., an iPhone, an Android operating phone, a Blackberry, a Window operating phone, etc.); a tablet computer (e.g., an iPad), and a personal digital assistant (PDA).

The reading device 104 can include a desktop computer, a laptop computer, and/or any other suitable devices operable to send and receive signals, store and retrieve data, and/or execute modules.

In some examples, the reading device 104 is configured a portable reader. Such a portable reading device 104 can be configured as an independent handheld device, or as a device that is connected to a movable clinical data station or equipment. As described herein, for home care, the reading device 104 can be various consumer mobile devices as described above. In other examples, the reading device 104 is mounted to a structure or device that the subject S periodically or continuously uses. For example, the reading device 104 is mounted to the sides or side rails of a hospital or homecare bed for a patient, such that the reading device 104 remains within, or easily comes into, a read range of the sensing patch 102 attached to the patient's body. In yet other examples, the reading device 104 is incorporated into, or used with, other monitoring systems, such as Connex® Vital Signs Monitor (CVSM) available from Welch Allyn Inc., Skaneateles Falls, N.Y. An example of the reading device 104 is described in more detail with reference to FIG. 11.

Referring still to FIG. 1, the data management system 106 operates to manage the subject's health conditions and other information. The data management system 106 can be operated by the healthcare practitioner and/or a healthcare service provider, such as a hospital or clinic. Some embodiments of the data management system 106 are configured to receive measurement data (and other data associated with the subject S) from the reading device 104, and analyze the data for various purposes. In some embodiments, the data management system 106 operates to provide information that can be used to assist the guardian and/or the healthcare practitioner to provide suitable healthcare to the subject S. In some examples, the data management system 106 includes such a computing device as described in FIG. 11. Examples of the data management system 106 include Connex® data management systems available from Welch Allyn Inc., Skaneateles Falls, N.Y.

As illustrated in FIG. 1, the wireless communication link 110 is established between the sensing patch 102 and the reading device 104. The data collected by the sensing patch 102 are wirelessly transmitted to the reading device 104 via the wireless communication link 110. The wireless communication link 110 can be established as short range wireless communication, such as radio frequency identification (RFID) communication, near field communication (NFC), Bluetooth communication, or Wi-Fi communication.

In some examples, the reading device 104 is configured as an active RFID reader and capable of communicating with the sensing patch 102, which correspondingly includes a RFID device (e.g., a RFID tag). When the reading device 104 is brought close enough to the sensing patch 102 attached to the subject S, a short-range RF communication is established between the sensing patch 102 and the reading device 104 via electromagnetic fields so that query, authorization/authentication, and/or data interchange processes are performed between the sensing patch 102 and the reading device 104.

In other examples, the reading device 104 includes a NFC interface for establishing radio communication with the sensing patch 102 by bringing the reading device 104 into proximity to the sensing patch 102 or touching the reading device 104 with the sensing patch 102. The NFC interface can be configured in a way known in the art. The sensing device 102 is correspondingly configured to communicate with the NFC interface of the reading device 104. As such, the reading device 104 operates as an NFC reader and the sensing device 102 functions as an NFC tag.

In yet other examples, the reading device 104 includes a Bluetooth communication interface to establish Bluetooth wireless connection with the sensing device 102. The Bluetooth communication interface can be configured in a way known in the art. The sensing device 102 is also configured to be capable of establish Bluetooth communication with the reading device 104. As such, the sensing device 102 and the reading device 104 can be correspondingly configured to transmit data via low-power radio waves.

In yet other examples, the reading device 104 includes a Wi-Fi communication interface to establish Wi-Fi connection with the sensing device 102. The Wi-Fi communication interface can be designed in a way known in the art. The sensing device 102 is also configured to communicate with the Wi-Fi communication interface of the reading device 104. As such, the sensing device 102 and the reading device 104 can be correspondingly configured to transmit data via radio waves. By way of non-limiting example, and as will be appreciated by those skilled in the relevant arts, Wi-Fi can be deployed in accordance with IEEE 802.11 (Wireless LAN), IEEE 802.15.4 (Low-Rate wireless PAN, such as ZigBee, WirelessHART, and MiWi), IEEE 802.22 (Wireless Regional Area Network), or other standard. In some embodiments, Wi-Fi connection can be alternatively established if other connections (e.g., RFID, NFC, and Bluetooth) are not established.

In other embodiments, the wireless communication link 110 can implement other types of short-range communications, such as infrared data communication, Z-Wave, ANT+, and other suitable protocols.

Although the wireless communication link 110 is primarily described in the present disclosure, other embodiments are also possible where a wired communication link replaces the wireless communication link 110 or used together with the wireless communication link 110.

With continued reference to FIG. 1, the data communication network 112 communicates digital data between one or more computing devices, such as among the reading device 104 and the data management system 106. Examples of the network 112 include a local area network and a wide area network, such as the Internet. In some embodiments, the network 112 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. A wireless communication system typically includes an optical or RF transmitter for transmitting optical or RF signals, and an optical or RF receiver for receiving optical or RF signals. Examples of wireless communication systems include Wi-Fi communication devices (such as utilizing wireless routers or wireless access points), cellular communication devices (such as utilizing one or more cellular base stations), and other wireless communication devices.

As such, since the sensing device 102 and the reading device 104 communicate with each other via the wireless communication link 110, the system 100 allows conveniently measuring physiological parameters without requiring the patient's involvement. For example, when a patent with the sensing device 102 is in sleep, a user can simply bring the reading device 104 close to the sensing device 102 to activate the sensing device 102 and/or receive the measurements from the sensing device 102 without waking the patient.

Figure 2:
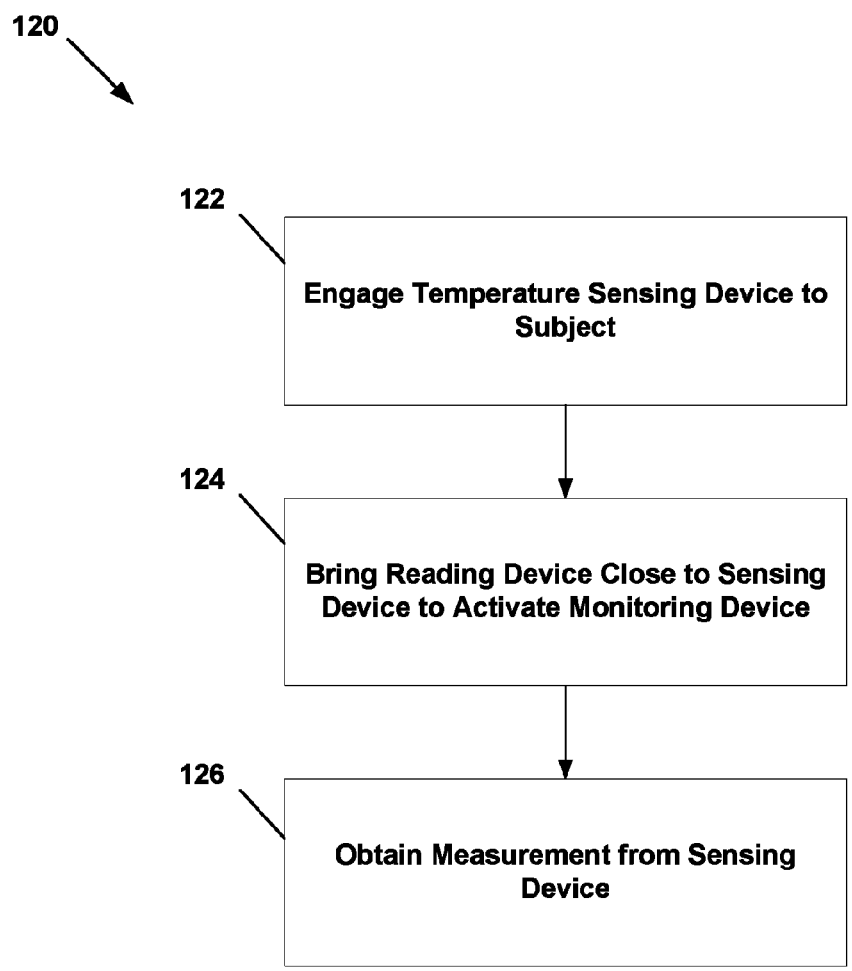
FIG. 2 is a flowchart illustrating an example method of operating the system of FIG. 1

FIG. 2 is a flowchart illustrating an example method 120 of operating the system 100 using the sensing device 102 and the reading device 104.

In the present disclosure, the sensing device 102 includes a patch that is removably attached on the body surface of the subject S and configured to monitor body temperature of the subject S. Therefore, the sensing device 102 is also referred to herein as a temperature sensing device or patch. Further, the sensing device 102 can communicate with the reading device 104 via the wireless communication link 110, such as short range wireless communication. Other embodiments are also possible in various manners.

At operation 122, the temperature sensing device 102 is engaged with the subject S. In some embodiments, the temperature sensing device 102 is configured as a patch and attached to the subject's skin so as to be ready for measuring the subject's body temperature.

At operation 124, the reading device 104 is brought close to the sensing device 102 within a predetermined activation range so that the sensing device 102 is activated. When activated, the sensing device 102 can operate to detect the temperature at a body area of the subject S on which the sensing device 102 is attached. Where the reading device 104 is configured as a passive device, the reading device 104 transmits a trigger signal to the sensing device 102 such that the sensing device 102 is supplied with electric power for activation.

At operation 126, the reading device 104 obtains the temperature measurement from the sensing device 102. For example, upon activation, the sensing device 102 measures the temperature and transmits the measurements to the reading device 104 via the wireless communication link 110. The operation 126 is further described below with reference to FIG. 7.

Figure 3:
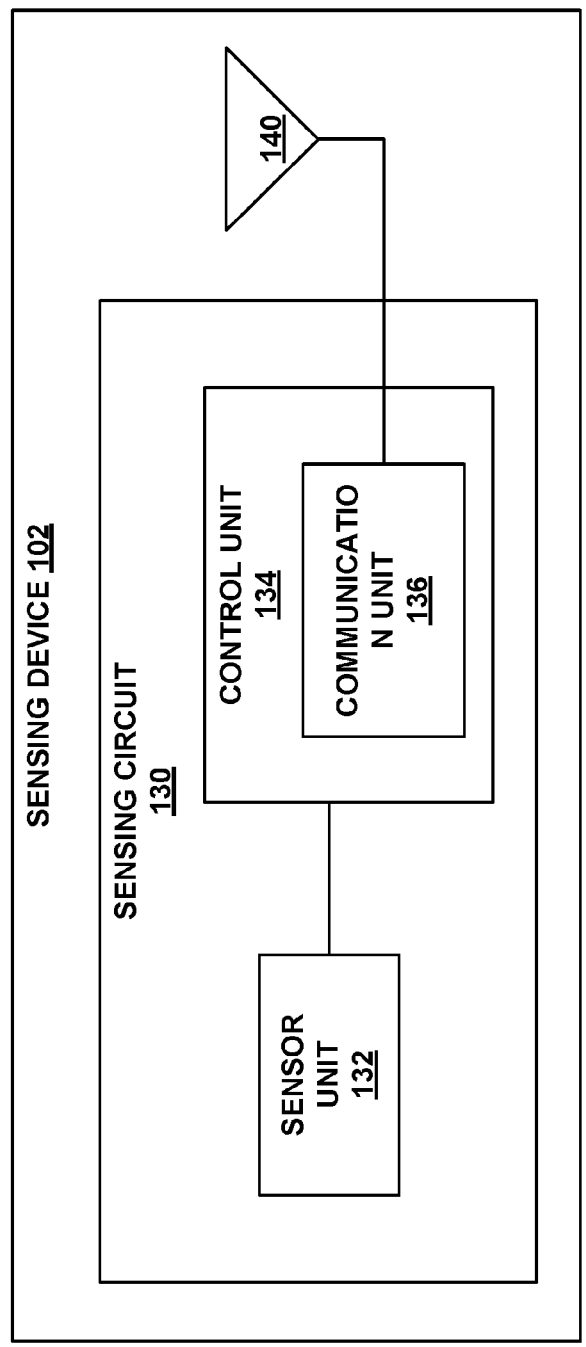
FIG. 3 schematically illustrates an example sensing device for sensing and transmitting physiological parameters in accordance with an exemplary embodiment of the present disclosure.

FIG. 3 schematically illustrates an example of the sensing device 102, which is used for sensing and transmitting physiological parameters of the subject S. The sensing device 102 includes a sensing circuit 130 and an antenna 140. The sensing circuit 130 can include a sensor unit 132, a control unit 134, and a communication unit 136.

In some embodiments, the sensing device 102 operates as a transponder configured to emit an identifying signal in response to an interrogating received signal. In the depicted example, the sensing device 102 is primarily illustrated as a near field communication (NFC) unit. In other embodiments, the sensing device 102 can be designed to be in other types of communication, such as radio frequency identification (RFID) unit, Bluetooth, Wi-Fi, and other short-range wireless communications.

Figure 5:
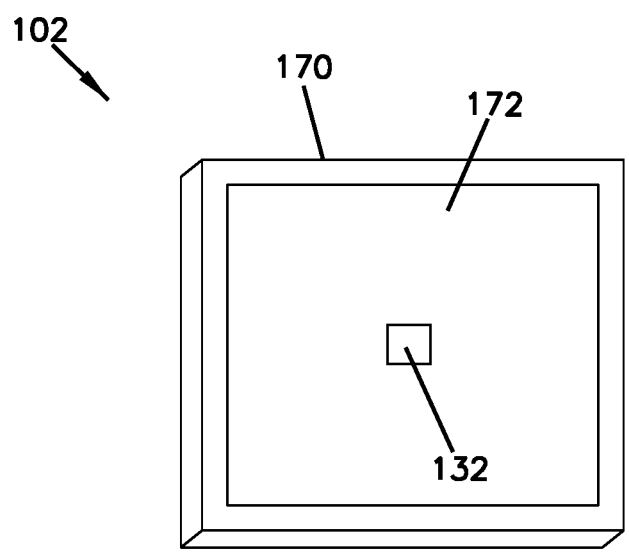
FIG. 5 is a schematic bottom view of the sensing device of FIG. 3.
Figure 6:
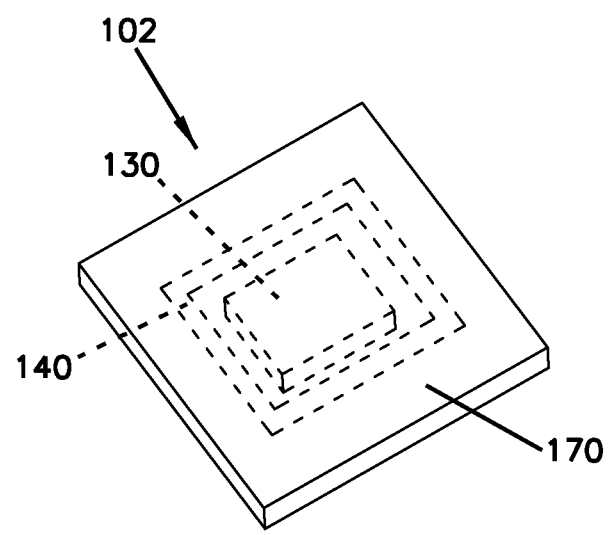
FIG. 6 is a schematic perspective view of the sensing device of FIG. 5.

As further illustrated in FIGS. 5 and 6, the sensing device 102 can be configured as a patch. The sensing circuit 130 can be designed as a tag or label suitable to be contained within the patch. The tag or label can be formed to be substantially flat and thin so as to be easily mounted onto, or embedded into, the patch.

The sensor unit 132 includes one or more sensors operable to detect one or more physiological parameters. In some examples, the sensor unit 132 includes one sensor for detecting one type of physiological parameters. In other examples, the sensor unit 132 includes a plurality of sensors for detecting different types of physiological parameters. Example sensors of the sensor unit 132 include temperature sensors, heartrate sensors, electrocardiogram (ECG) sensors, respiratory rate sensors, accelerometers, SpO2 sensors, heartrate variability sensors, galvanic skin response sensors, blood pressure sensors, blood glucose sensors, blood oxygen sensors, and any other sensors suitable for measuring physiological parameters. The sensor unit 132 can further include one or more sensors (e.g., accelerometer) for detecting the subject's activity and posture, such as whether the subject is standing, sitting, laying down, or engaged in physical activity, such as running.

Where the sensor unit 132 is configured to detect temperature, the sensor unit 132 can include at least one temperature responsive element, such as a thermistor, thermocouple, or other miniature temperature responsive sensor. In other examples, the sensor unit 132 includes an infrared thermometer capable of sensing the infrared radiation emitted near the skin or other external surface of a patient. Other types of thermometers are also possible.

The control unit 134 operates to process signals obtained by the sensor unit 132. Data processed by the control unit 134 can be stored in a storage unit. In some examples, the storage unit can also store information for identifying the sensing device 102, such as serial information or tag information. When the parameter data (e.g., measurement data) can be transmitted from the sensing device 102 to the reading device 104, the device identification information can also be transmitted to the reading device 104 for identifying the sensing device 102 in communication. An example of the control unit 134 is further described with reference to FIG. 4.

The communication unit 136 operates to send signals obtained by the sensor unit 132 to the reading device 104 via the wireless communication link 110. In some examples, the communication unit 136 can also receive signals from the reading device 104 via the wireless communication link 110. In other examples, the communication unit 136 is further configured to communicate with the data management system 106 and/or other computing devices via the network 112. Although the communication unit 136 is illustrated to be included in the control unit 134, the communication unit 136 can be configured separately from the control unit 134.

The antenna 140 is configured to receive and transmit a radio frequency (RF) signal. The antenna 140 can be made flat so as to be incorporated into the sensing patch 102. In some example, the antenna 140 is separate from the sensing circuit 130. In other embodiments, the antenna 140 can be formed on the sensing circuit 130.

Figure 4:
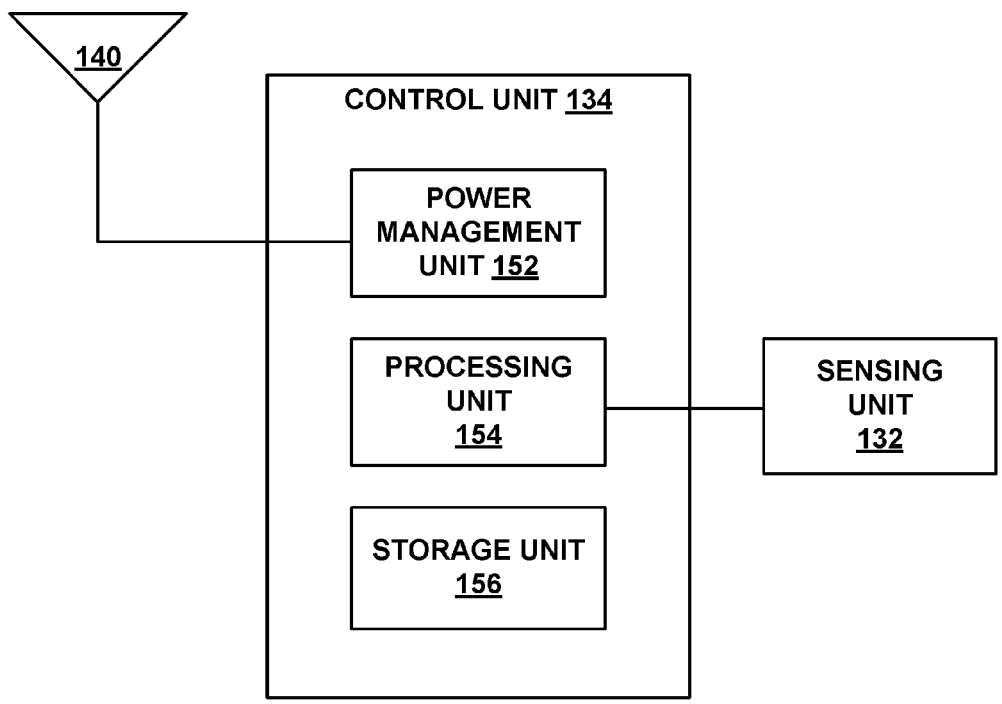
FIG. 4 schematically illustrates an example control unit of the sensing device of FIG. 3.

FIG. 4 schematically illustrates an example of the control unit 134 of FIG. 3. In the illustrated example, the control unit 134 is configured for NFC or RFID communication.

The control unit 134 is arranged within the sensing patch 102 and electrically coupled to the antenna 140. In some embodiments, the control unit 134 is implemented in an integrated circuit (IC). In operation, a signal is received by the antenna 140 and communicated to the control unit 134. The control unit 134 operates to harvest power and respond as necessary in response to the incoming signal. In particular, the control unit 134 is configured to store and process information, modulate and demodulate a RF signal, collect power from an associated reader signal, and perform other functions.

In some embodiments, the control unit 134 includes a power management unit (PMU) 152, a processing unit 154, and a storage unit 156. In other embodiments, the control unit 134 can include one or more components in addition to the components described above, and/or replace one or more of the components described above by different components.

The PMU 152 operates to harvest raw RF power received via the antenna 140. In particular, an RF wave received via the antenna 140 is transmitted to the PMU 152 as a signal. The signal is used for harvesting the power and also decoded for further processes. Where the sensing patch 102 is implemented as a passive NFC device, the sensing patch 102 does not have its own power source. The sensing patch 102 can be powered by electromagnetic induction from magnetic fields produced near a reader of the sensing patch 102 (e.g., the reading device 104). However, it is recognized that the control unit 134 can be powered in different manners. For example, where the sensing patch 102 is implemented as an active or semi-passive RFID tag, the sensing patch 102 uses internal power source to power the circuit.

The processing unit 154 operates to receive signals from the antenna 140. In some examples, a demodulator is provided to demodulate an RF signal received via the antenna 140. The demodulator can be implemented in a way known in the art, including, for example, attenuator stage and amplifier stage. The processing unit 154 can perform various operations and generate an output signal for transmission. In some examples, a modulator is provided to modulate an output signal generated by the processing unit 154. The modulated signal is transmitted through the antenna 140 to one or more readers, such as the reading device 104. The modulator can be implemented in a way known in the art, including, for example, driver stage and amplifier stage. The processing unit 228 can be implemented in a way known in the art, including, for example, a processor, a decoder, and an encoder.

The storage unit 156 includes one or more memories configured to store data readable by a reader, such as the reading device 104. The storage unit 156 can be of various types, including volatile and nonvolatile, removable and non-removable, and/or persistent media. In some embodiments, the storage unit 156 is an erasable programmable read only memory (EPROM).

Referring to FIGS. 5 and 6, an example of the sensing device 102 is described in more detail. FIG. 5 is a schematic bottom view of the sensing device 102 in accordance with an exemplary embodiment of the present disclosure, and FIG. 6 is a schematic perspective view of the sensing device 102 of FIG. 5.

In some examples, the sensing device 102 is manufactured as a single piece. The sensing device 102 can be configured to be disposable or for a single subject use. In the illustrated example, the sensor device 102 includes a flexible substrate 170 that includes the sensing circuit 130 and the antenna 140 therewithin. The substrate 170 can expose at least a portion of the sensor unit 132, such as a thermistor acting as a temperature responsive element, therethrough so that the sensor unit 132 is located closer to the subject's body surface when the sensing device 102 is attached to the subject's body. In other embodiments, other types of sensor unit 132 can be employed.

In some examples, an adhesive layer 172 is provided on the substrate 170 to allow the substrate 170 to be attached to a body surface of the subject S. In other examples, the substrate 170 is adapted to be removably attached to a body surface of the subject S with or without the adhesive layer 172. In some examples, the substrate 170 is made of flexible materials, such as polymeric materials, which are stretchable to remain attached to a body skin when the body skin deforms.

The adhesive layer 172 can be made of various materials. In some examples, the adhesive layer 172 is made of flexible polymeric materials, which are stretchable to conform to the deformation of a body skin on which the sensing patch 102 is attached. The adhesive layer 172 can include a hydrogel, which can provide skin-adhesion properties. The adhesive layer 172 can further function as a thermal conduit between the sensor unit 132 and the subject's skin. In addition or alternatively, the adhesive layer 172 includes a pressure-sensitive adhesive.

The materials used for the layers of the sensing patch 102 are capable of providing resistance to water, sweat, humidity, and other human or environmental factors that may reduce or deteriorate the bond between the patch 102 and the subject's skin over the length of a predetermined time period.

In some examples, the layers of the sensing patch 102 are made to be flexible and stretchable to accommodate the movement of a body skin of the subject S to which the sensing patch 102 is attached. As such, when the body skin moves or changes its shape (e.g., the body skin stretches or shrinks), the layers of the sensing patch 102 can remain properly attached to the body skin by conforming to the various shapes of the body skin. Since the sensing circuit 130 is small in size relative to the sensing patch 102, the sensing circuit 130 does not generally interfere with the flexibility of the layers of the sensing patch 102. In other examples, the sensing circuit 130 can also be made with a flexible circuit board so that the layers and the sensing circuit 130 of the sensing patch 102 conform to different shapes of the subject's body skin on which the sensing patch 102 is attached.

Figure 7:
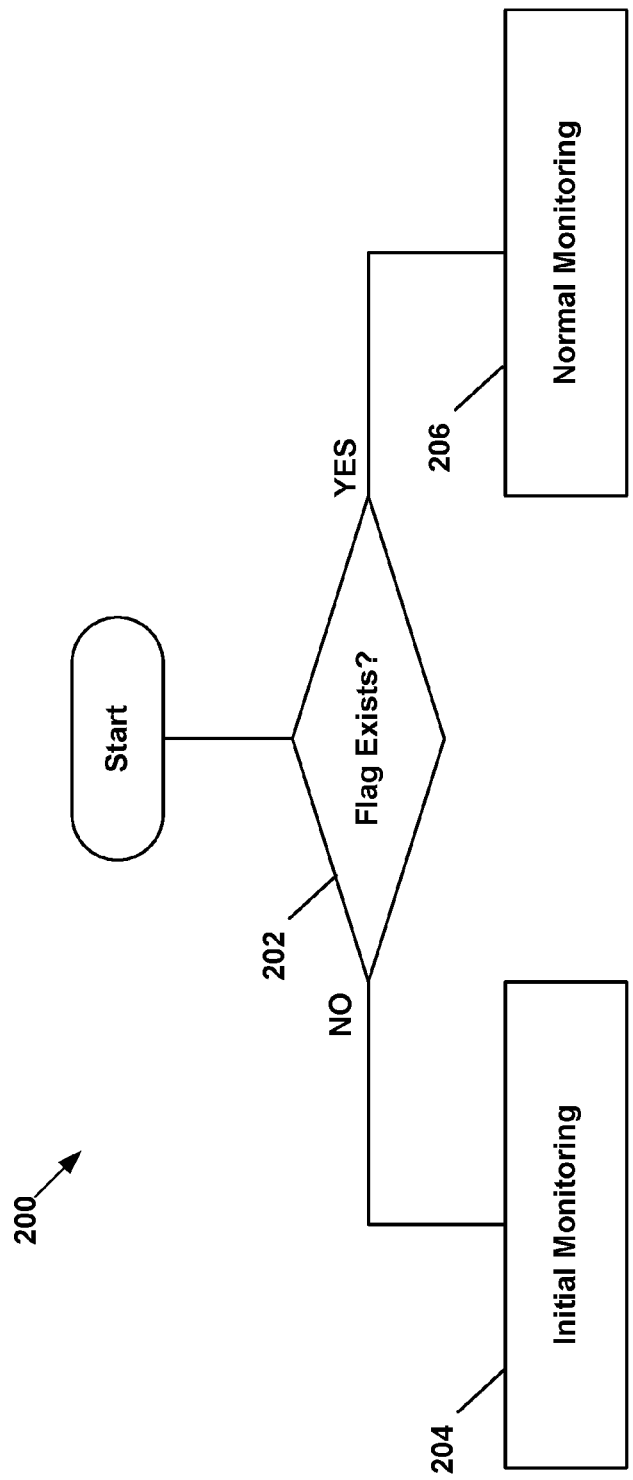
FIG. 7 is a flowchart illustrating an example method of obtaining a physiological measurement in accordance with an exemplary embodiment of the present disclosure.
Figure 11:
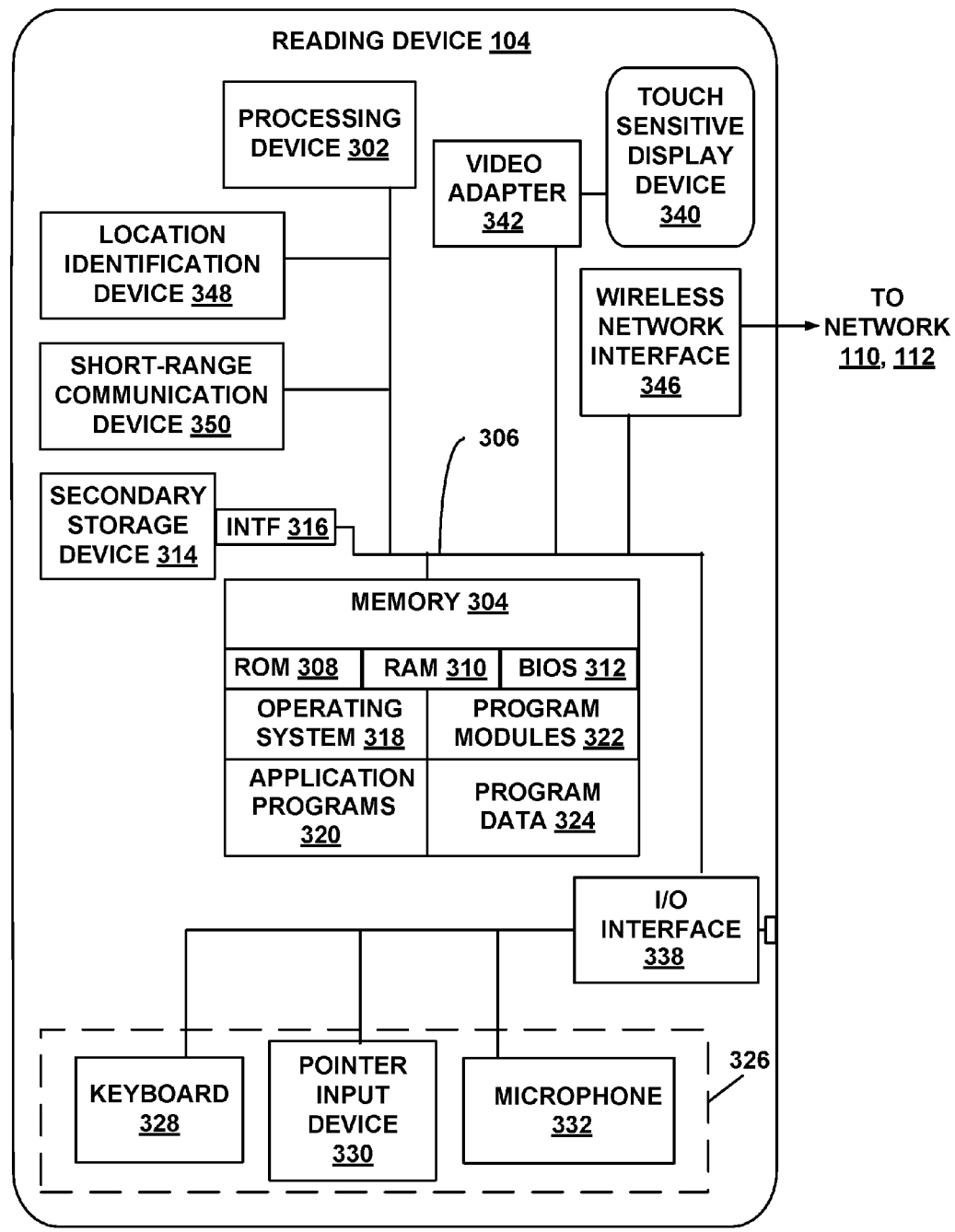
FIG. 11 illustrates an exemplary architecture of a reading device of the system of FIG. 1.

FIG. 7 is a flowchart illustrating an example method 200 of obtaining a physiological measurement using the physiological parameter sensing device 102 and the reading device 104 in accordance with an exemplary embodiment of the present disclosure. In some examples, the method 200 includes operations that are performed by the reading device 104 that is in communication with the sensing device 102. For example, the operations in the method 200 are executed by one or more processors, such as the processing device 302 as illustrated in FIG. 11. In other examples, the method 200 includes operations that are at least partially performed by the sensing device 102.

The method 200 begins when the sensing device 102 is arranged in place on a predetermined location of the subject's body and activated by the reading device 104. As described above, the sensing device 102 can be activated when the reading device 104 comes in proximity of the sensing device 102 and falls within a predefined reading range.

Figure 9:
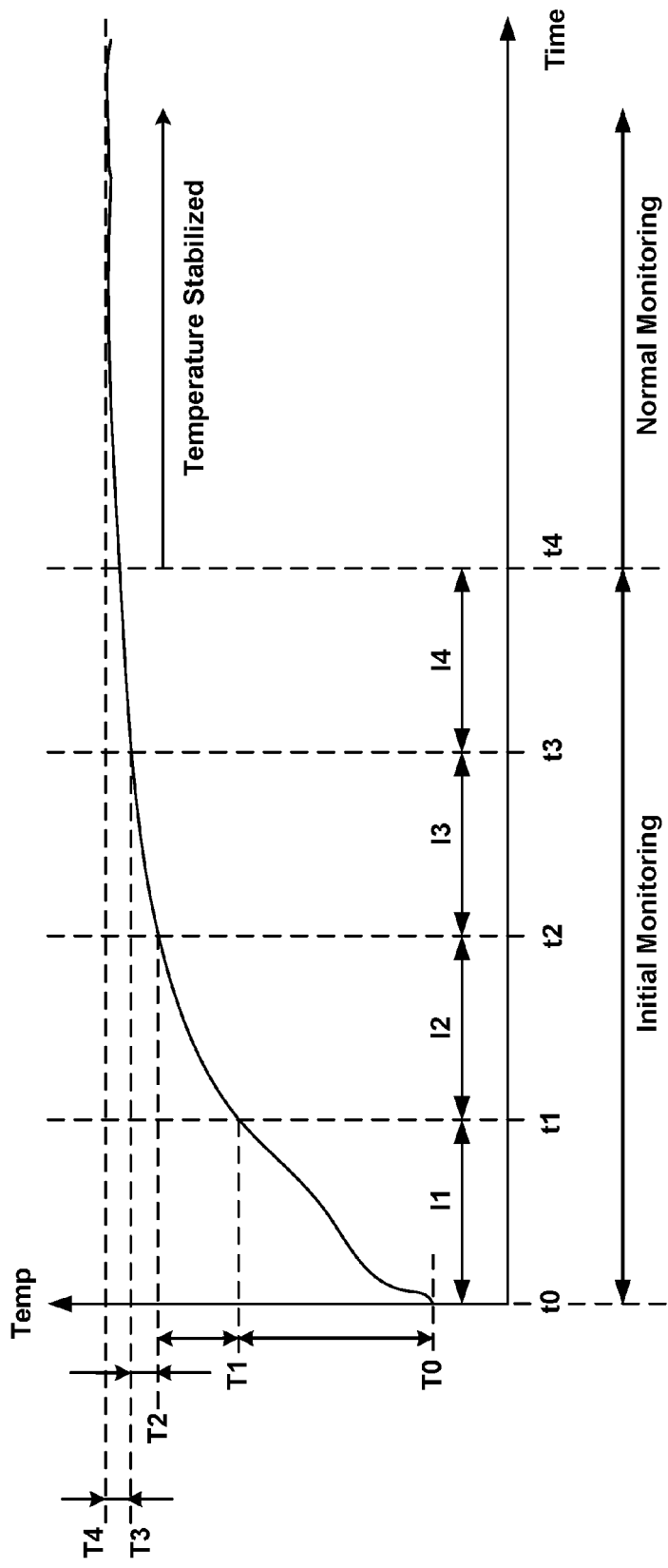
FIG. 9 illustrates a variation in detected body temperature over time.

At operation 202, the reading device 104 determines if a flag for indicating the stability of the sensing device 102 is stored in the sensing device 102. The stability indication flag is used to represent that the temperature to be detected by the sensing device 102 has been stabilized over time, and that the sensing device 102 is thus adapted to instantly provide an accurate temperature measurement without any time delay in measuring a temperature through the sensing device 102. As described herein, the sensing device 102 is not ready to immediately detect the body temperature of the subject S shortly after the sensing device 102 is first attached to a body portion (e.g., skin or tissues) of the subject S. Such measurement time delay can occur for various reasons. For example, such reasons can include the construction of the sensing device 102 including the location of the sensing unit 132 within the sensing device 102, the heat capacity of the sensing unit 132, a difference in temperature between the sensing device 102 and the subject's body portion to which the sensing device 102 is attached, and an improper attachment of the sensing device 102 on the subject's body portion. Because of such various reasons, when the sensing device 102 is first engaged with the subject's body, the temperature detected by the sensing device 102 can be unstable or fluctuate for certain period of time (e.g., t3 or t4 as illustrated in FIG. 9) until the sensing device 102 becomes in thermal equilibrium with the body portion on which the sensing device 102 is attached. As the sensing device 102 and the body portion engaging the sensing device 102 become in thermal equilibrium, the temperature detected by the sensing device 102 is stabilized, and thus can be used as an accurate measurement of the subject's body temperature.

As such, the sensing device 102 typically requires some time until it can reliably measure the body temperature. However, it is preferable to take body temperature measurements as quickly as possible in many situations. An indication of temperature stability is important to shorten the time required to measure a reliable body temperature. As such, the stability indication flag can be adapted to provide such an indication of temperature stability. As described herein, if it is indicated that the temperature detected by the sensing device 102 has been stabilized, the reading device 104 can obtain the body temperature measurement immediately (i.e., without an extended period of time for stabilization) when the sensing device 102 is activated to detect the body temperature. If it is found that the temperature detected by the sensing device 102 is not stabilized yet, the reading device 104 can be configured to predict the body temperature for quick body temperature reading. In this case, the reading device 104 can be further configured to set a stability indication flag for quick response in subsequent measurements. The details are further described below with reference to FIGS. 8-10.

In some examples, the stability indication flag is implemented as a predefined bit or bit sequence that holds a binary value, and stored in the storage unit 156 of the sensing device 102. When the reading device 104 activates the sensing device 102, the sensing device 102 can transmit data including the flag so that the reading device 104 determines the existence of the flag. In other examples, the stability indication flag can be stored in other devices, such as the reading device 104.

If it is determined that the stability indication flag is not present, the method 200 moves on to an initial monitoring operation 202. As described below, the stability indication flag is set during the initial monitoring operation 204. If the stability indication flag is determined to be present, a normal monitoring operation 204 is performed. An example of the initial monitoring operation 202 is described with reference to FIG. 8. An example of the normal monitoring operation 206 is described with reference to FIG. 10.

Although the operations 202, 204, and 206 are described to be performed primarily by the reading device 104 above, the sensing device 102 can be configured to perform at least one of the operations in other embodiments.

Figure 8:
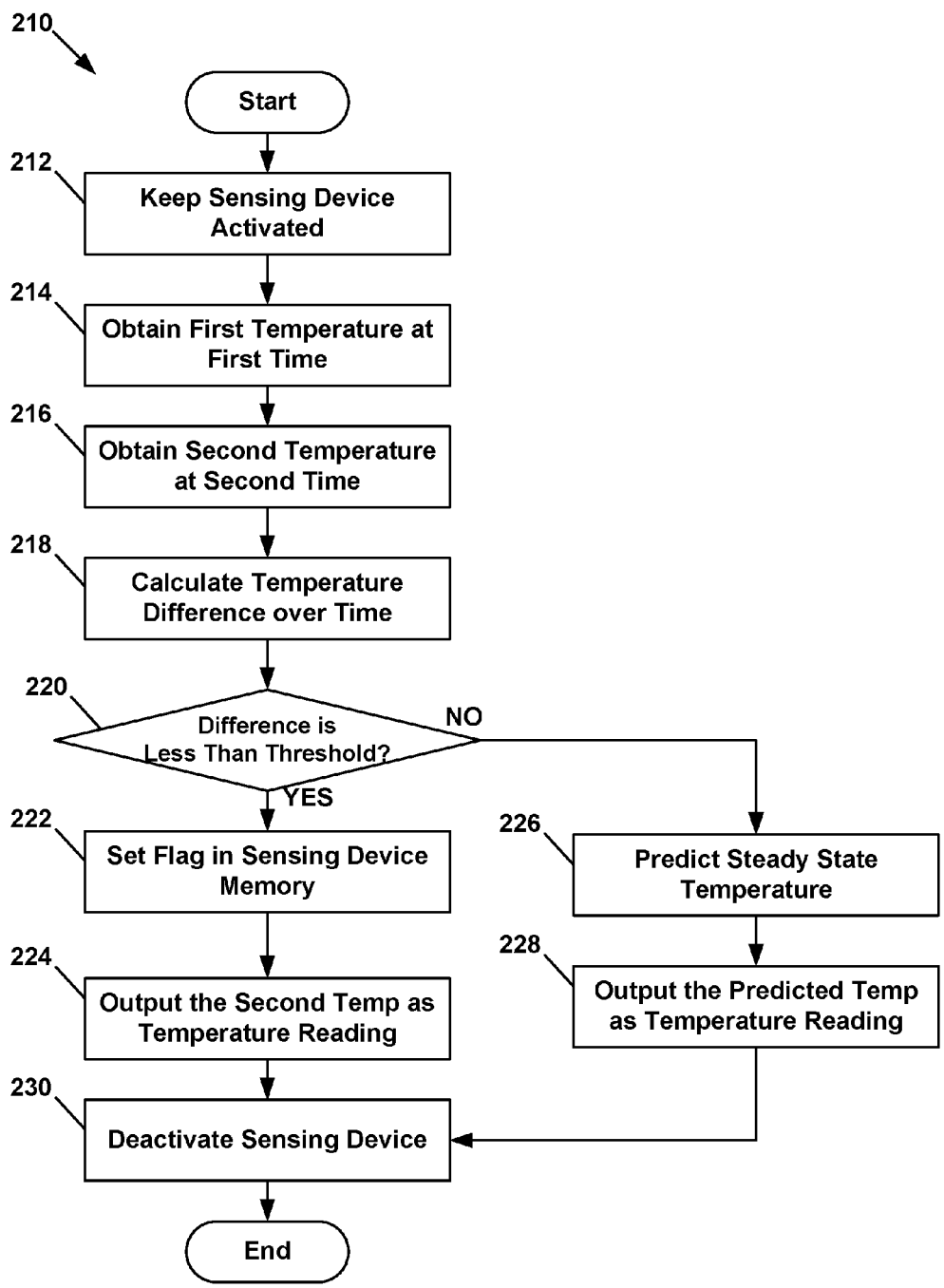
FIG. 8 is a flowchart illustrating an example method of performing an initial monitoring operation of the method of FIG. 7.

FIG. 8 is a flowchart illustrating an example method 210 of performing the initial monitoring operation 204. The method 210 is described with further reference to FIG. 9, which illustrates a variation in detected body temperature (T) over time (t).

In some examples, the method 210 includes operations that are performed by the reading device 104 that is in communication with the sensing device 102. For example, the operations in the method 210 are executed by one or more processors, such as the processing device 302 as illustrated in FIG. 11. In other examples, the method 210 includes operations that are at least partially performed by the sensing device 102.

In general, during the initial monitoring operation 202, the reading device 104 obtains at least two temperatures at different times, determines a rate of temperature increase, and compare the rate with a predetermined threshold to indicate that the temperature to be monitored has been sufficiently stabilized to provide a reliable reading.

The method 210 is performed when the reading device 104 activates the sensing device 102 (i.e., the operation 124 in FIG. 2) and while the reading device 104 keeps the sensing device 102 activated, as illustrated at operation 212. The sensing device 102 stays activated for a predetermined period of time for the initial monitoring operation 202. The predetermined period of time is longer than a time required for performing the normal monitoring operation 204. In some embodiments, the predetermined period of time is between about 1 second and about 10 seconds. In other embodiments, the predetermined period of time is between about 2 seconds and about 6 seconds. In yet other embodiments, the predetermined period of time is between about 3 seconds and about 5 seconds. In yet other embodiments, the predetermined period of time is set about 4 seconds.

At operation 214, the reading device 104 operates to obtain a first temperature at a first time. In some examples, the reading device 104 sends a request for detecting a temperature at the first time, and, in response, the sensing device 102 transmits the temperature (i.e., the first temperature) detected at the first time. In other examples, the sensing device 102 is programmed to automatically detect temperature at a plurality of times at predetermined intervals during the initial monitoring operation 204 (i.e., when the stability indication flag is not present), and, therefore, the sensing device 102 can transmit the first temperature at the first time to the reading device 104 as programmed. Other methods for obtaining the temperature at predetermined times are also possible in yet other examples.

At operation 216, the reading device 104 operates to obtain a second temperature at a second time. The second temperature at the second time can be detected and transmitted to the reading device 104 similarly to the operation 214.

By way of example, the first time in the operation 214 is set as a time (i.e., t0 in FIG. 9) at which, or shortly after, the sensing device 102 is activated. The second time in the operation 216 is set as a predetermined time (i.e., t1 in FIG. 9) after the sensing device 102 is activated. In other examples, the first and second times can be different points in time at different intervals after the sensing device 102 is activated. For example, in FIG. 9, the first and second times can be any combination selected from t0, t1, t2, and t3, and t4 to the extent that the first time is ahead of the second time.

At operation 218, the reading device 104 operates to calculate a difference between the first temperature and the second temperature over time. The difference represents a variation slope of the monitored temperature. In the above example, the difference can be calculated as $$\frac{T1 - T0}{t1 - t0}.$$

At operation 220, the reading device 104 compares the difference calculated at the operation 218 with a predetermined threshold. In some examples, the reading device 104 determines whether the difference is less than the threshold. The threshold is determined to represent that the temperature is so stabilized over time as to provide a reliable reading on the body temperature. As the threshold is set to close to zero, the stability of the temperature over time increases.

If it is determined that the difference is less than the threshold ("YES" at the operation 220), the method 210 continues on to operation 222. Otherwise ("NO" at the operation 220), the method 210 moves on to operation 226.

At operation 222, the reading device 104 set a stability indication flag in the storage unit of the sensing device 102. As described herein, the stability indication flag is used to represent that the temperature to be detected by the sensing device 102 has been stabilized and thus the reading device 104 can take the body temperature measurement from the sensing device 102 immediately when the reading device 104 activates the sensing device 102. The stability indication flag is used at the operation 202 (FIG. 7) to determine which process is performed between the initial monitoring operation 204 and the normal monitoring operation 206. When the stability indication flag is found in subsequent measurements (i.e., the normal monitoring operation 206), the measurements can be quickly performed without any delay. In some examples, such a measurement can be taken in less than one second.

At operation 224, the reading device 104 outputs the second temperature as a body temperature reading for the subject S. In some examples, the predicted temperature is displayed on the reading device 104. In other examples, the predicted temperature is transmitted from the reading device 104 to the data management system 106 for further use.

At operation 226, the reading device 104 operates to predict a body temperature based on the temperatures detected in the preceding operations. The body temperature is predicted to save the measurement time during the initial monitoring operation 204. Therefore, a quick body temperature reading is possible even in the initial monitoring operation 204. In some examples, the body temperature is predicted based on the change in the temperature difference calculated in the operation 218. One example of the prediction process is described in U.S. Pat. No. 5,632,555, titled Medical Thermometer, assigned to Welch Allyn, Inc.

At operation 228, the reading device 104 outputs the predicted temperature as a body temperature reading for the subject S. In some examples, the predicted temperature is displayed on the reading device 104. In other examples, the predicted temperature is transmitted from the reading device 104 to the data management system 106 for further use.

At operation 230, the reading device 104 deactivates the sensing device 102 to finish the initial monitoring operation 204. In some examples, where the reading device 104 is a hand-held passive device, the reading device 104 is moved away from the sensing device 102 so as to be located outside the reading range, and the sensing device 102 loses power supply and is deactivated. Other methods for deactivating the sensing device 102 are possible in other embodiments.

Referring again to FIG. 9, the points in time (e.g., t0, t1, t2, t3, and t4) at which the temperature is measured by the sensing device 102 during the initial monitoring operation are configured to be apart at constant intervals (I1, I2, I3, and I4). During each interval, the temperature difference (T1-T0, T2-T1, T3-T2, and T4-T3) is evaluated to determine the variation in the temperature difference is stabilized. Depending on the threshold, it is interpreted that the temperature is stabilized over time. In the illustrated example, the temperature monitored after a time (t4) is considered to be stable. Thus, the stability indication flag is stored in the sensing device 102 after the time (t4), and the normal monitoring operation 206 can be performed after the time (t4). In other examples, the threshold can be set such that the temperature after a different time (e.g., t1, t2 or t3) is considered to be stabilized.

Figure 10:
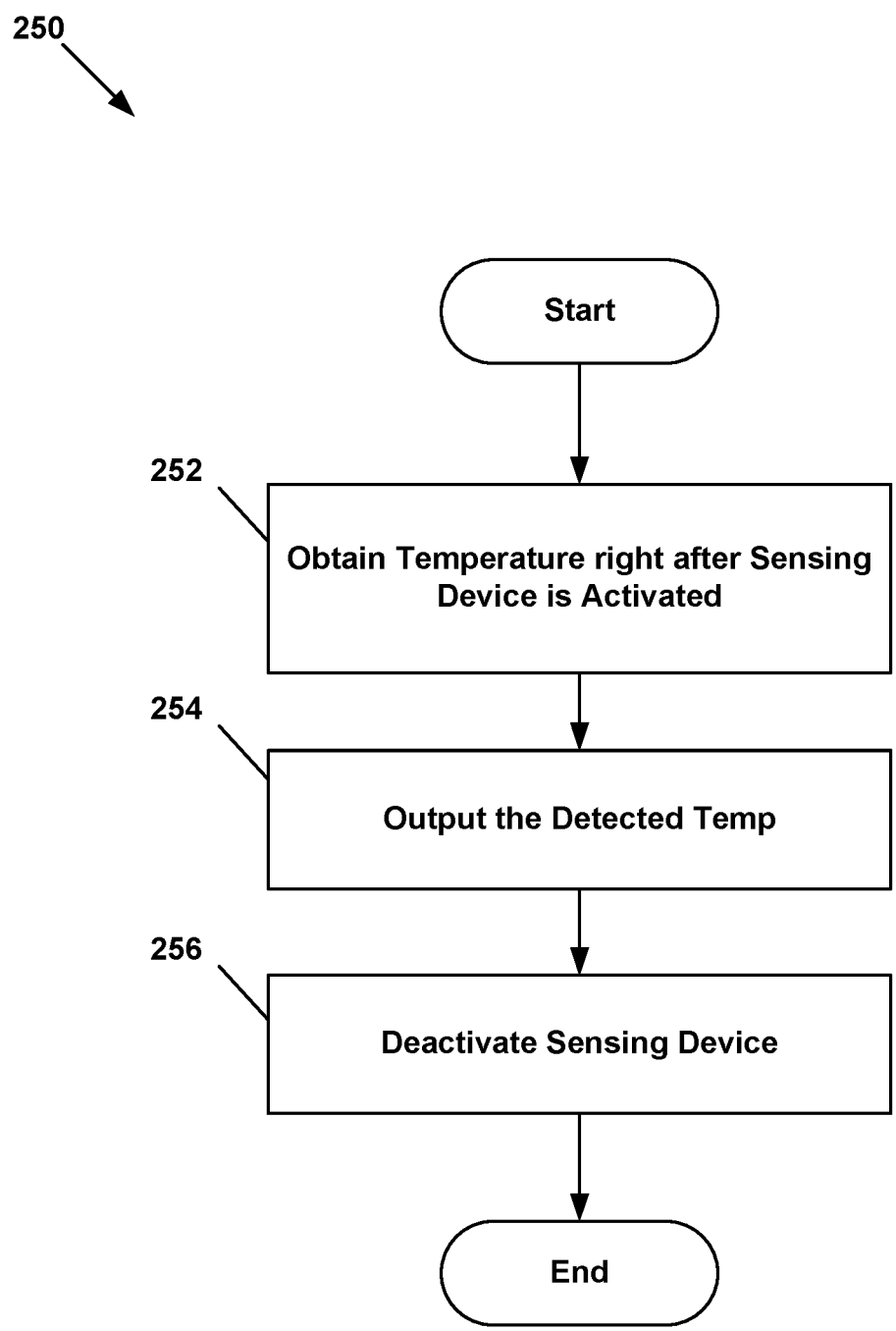
FIG. 10 is a flowchart illustrating an example method of performing a normal monitoring operation of the method of FIG. 7.

FIG. 10 is a flowchart illustrating an example method 250 of performing the normal monitoring operation 206. In some examples, the method 250 includes operations that are performed by the reading device 104 that is in communication with the sensing device 102. For example, the operations in the method 250 are executed by one or more processors, such as the processing device 302 as illustrated in FIG. 11. In other examples, the method 250 includes operations that are at least partially performed by the sensing device 102.

The method 250 is performed when the reading device 104 is activated (i.e., the operation 124 in FIG. 2) and the stability indication flag is found to be stored in the sensing device 102.

At operation 252, the reading device 104 obtains the temperature as soon as the sensing device 102 is activated. In some examples, the trigger signal that is transmitted from the reading device 104 to the sensing device 102 for activation can include a request for the sensing device 102 to detect the temperature using the sensing unit 132 thereof. Then, the sensing device 102 detects the temperature through the sensing unit 132 and transmits the measurement to the reading device 104 as the sensing device 102 is activated. In other examples, the sensing device 102 can be programmed to immediately detect and transmit the temperature to the reading device 104 when activated.

As such, obtaining the body temperature during the normal monitoring operation can be completed in a shorter period of time than the temperature measuring process during the initial monitoring operation. In some examples, during the normal monitoring operation, the temperature can be obtained in less than four seconds after the sensing device 102 is activated. In other examples, during the normal monitoring operation, the temperature can be obtained in less than 2 seconds after the sensing device 102 is activated. In yet other examples, the temperature can be obtained in less than a second after the sensing device 102 is activated for the normal monitoring operations.

At operation 254, the reading device 104 receives the detected measurement of the body temperature and outputs the measurement. In some examples, the detected temperature is displayed on the reading device 104. In other examples, the temperature is transmitted from the reading device 104 to the data management system 106 for further use.

At operation 256, the reading device 104 deactivates the sensing device 102 to finish the normal monitoring operation 204. In some examples, where the reading device 104 is a hand-held passive device, the reading device 104 is moved away from the sensing device 102 so as to be located outside the reading range, and the sensing device 102 loses power supply and is deactivated. Other methods for deactivating the sensing device 102 are possible in other embodiments.

As such, once the stability indication flag is set in the sensing device 102, the normal monitoring operation 206 is executed by the reading device 104 and the body temperature of the subject S can be instantly obtained as the reading device 104 activates the sensing device 102. When the measurement is obtained, the sensing device 102 is deactivated until the next measurement is requested by the reading device 104. Since the stability indication flag has been set up, the subsequent measurements can also be immediately obtained each time the sensing device 102 are activated.

In some examples, the reading device 104 can be configured to periodically activate the sensing device 102 to obtain a plurality of body temperatures over time. For example, where the reading device 104 is configured with a fixed structure, such as a hospital bed or homecare bed, so as to be located close to the sensing device 102 within a read coverage, the reading device 104 is designed to transmit a trigger signal to the sensing device 102 for activation at predetermined intervals.

Although it is primarily described herein that the sensing device 102 is configured as a passive device, which is activated by the reading device 104, it is also possible to configure the sensing device 102 as an active device, which includes its own power source, such as a battery. In this structure, the sensing device 102 can be configured to periodically detect the body temperature of the subject S without requiring a trigger signal from the reading device 104. In some examples, the active sensing device 102 can be configured to determine the temperature rise or stability (such as the initial monitoring operation 204) without interaction with the reading device 104. Further, the active sensing device 102 can automatically set reading intervals based on the temperature rise or stability. In other examples, the active sensing device 102 can extend the reading intervals longer when the temperature is determined to have been stabilized (i.e., the sensing device has reached thermal equilibrium). Such extended reading intervals can reduce computing process and save the power source (e.g., a battery of the sensing device 102).

FIG. 11 illustrates an exemplary architecture of the reading device 104. The reading device 104 illustrated in FIG. 11 is used to execute the operating system, application programs, and software modules (including the software engines) described herein.

The reading device 104 is a computing device of various types. In some embodiments, the reading device 104 is a mobile computing device. Examples of the reading device 104 as a mobile computing device include a mobile device (e.g., a smart phone and a tablet computer), a wearable computer (e.g., a smartwatch and a head-mounted display), a personal digital assistant (PDA), a handheld game console, a portable media player, a ultra-mobile PC, a digital still camera, a digital video camera, and other mobile devices. In other embodiments, the reading device 104 is other computing devices, such as a desktop computer, a laptop computer, or other devices configured to process digital instructions.

It is recognized that the architecture illustrated in FIG. 11 can also be implemented in other computing devices used to achieve aspects of the present disclosure. For example, the data management system 106 can be configured similarly to the architecture of FIG. 11. To avoid undue repetition, this description of the reading device 104 will not be separately repeated herein for each of the other computing devices including the data management system 106.

The reading device 104 includes, in some embodiments, at least one processing device 302, such as a central processing unit (CPU). A variety of processing devices are available from a variety of manufacturers, for example, Intel or Advanced Micro Devices. In this example, the reading device 104 also includes a system memory 304, and a system bus 306 that couples various system components including the system memory 304 to the processing device 302. The system bus 306 is one of any number of types of bus structures including a memory bus, or memory controller; a peripheral bus; and a local bus using any of a variety of bus architectures.

The system memory 304 includes read only memory 308 and random access memory 310. A basic input/output system 312 containing the basic routines that act to transfer information within the reading device 104, such as during start up, is typically stored in the read only memory 308.

The reading device 104 also includes a secondary storage device 314 in some embodiments, such as a hard disk drive, for storing digital data. The secondary storage device 314 is connected to the system bus 306 by a secondary storage interface 316. The secondary storage devices and their associated computer readable media provide nonvolatile storage of computer readable instructions (including application programs and program modules), data structures, and other data for the reading device 104.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 314 or memory 304, including an operating system 318, one or more application programs 320, other program modules 322, and program data 324.

In some embodiments, the reading device 104 includes input devices to enable a user to provide inputs to the reading device 104. Examples of input devices 326 include a keyboard 328, a pointer input device 330, a microphone 332, and a touch sensitive display 340. Other embodiments include other input devices. The input devices are often connected to the processing device 302 through an input/output interface 338 that is coupled to the system bus 306. These input devices 326 can be connected by any number of input/output interfaces, such as a parallel port, serial port, game port, or a universal serial bus. Wireless communication between input devices and interface 338 is possible as well, and includes infrared, BLUETOOTH® wireless technology, 802.11a/b/g/n, cellular, or other radio frequency communication systems in some possible embodiments.

In this example embodiment, a touch sensitive display device 340 is also connected to the system bus 306 via an interface, such as a video adapter 342. The touch sensitive display device 340 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 340, the reading device 104 can include various other peripheral devices (not shown), such as speakers or a printer.

When used in a local area networking environment or a wide area networking environment (such as the Internet), the reading device 104 is typically connected to the network through a network interface, such as a wireless network interface 346. Other possible embodiments use other communication devices. For example, some embodiments of the reading device 104 include an Ethernet network interface, or a modem for communicating across the network.

The reading device 104 typically includes at least some form of computer-readable media. Computer readable media includes any available media that can be accessed by the reading device 104. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the reading device 104. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 11 is also an example of programmable electronics, which may include one or more such computing devices, and when multiple computing devices are included, such computing devices can be coupled together with a suitable data communication network so as to collectively perform the various functions, methods, or operations disclosed herein.

Referring again to FIG. 11, the reading device 104 can include a location identification device 348. The location identification device 348 is configured to identify the location or geolocation of the reading device 104. The location identification device 348 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Referring again to FIG. 11, the reading device 104 further includes a short-range wireless communication device 350. The short-range wireless communication device 350 is configured to establish short-range wireless communication with the sensing patch 102. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. A system for monitoring a physiological parameter of a subject, the system comprising:
   a parameter sensing device attachable to a body of the subject, the parameter sensing device configured to detect at least one physiological parameter when attached to the body of the subject and activated, and
   a reading device configured to:
   transmit a trigger signal to the parameter sensing device to activate the parameter sensing device;
   obtain a first physiological parameter at a first time using the parameter sensing device;
   obtain a second physiological parameter at a second time using the parameter sensing device, the second time being later than the first time;
   calculate a parameter difference between the first physiological parameter and the second physiological parameter;
   compare the parameter difference with a threshold;
   if the parameter difference is less than the threshold, store a stability indication flag in the parameter sensing device, the stability indication flag adapted for indicating that the physiological parameter has stabilized over time; and
   if the parameter difference is less than the threshold, output the second physiological parameter as a detected parameter.

2. The system of claim 1, wherein the reading device is further configured to:
   if the parameter difference is not less than the threshold, predict a stabilized parameter before the physiological parameter is stabilized over time; and
   output the stabilized parameter as a detected parameter.

3. The system of claim 1, wherein the reading device is further configured to deactivate the parameter sensing device.

4. The system of claim 1, wherein the reading device is configured to maintain the parameter sensing device to be activated for a first period of time.

5. The system of claim 4, wherein the reading device is further configured to:
   transmit a second trigger signal to the parameter sensing device to activate the parameter sensing device;
   determine that the stability indication flag is stored in the parameter sensing device; and
   obtain a third parameter shortly after the parameter sensing device is activated.

6. The system of claim 5, wherein the reading device is configured to obtain the third parameter within a second period of time after the parameter sensing device is activated by the second trigger signal, the second period of time being shorter than the first period of time.

7. The system of claim 1, wherein the parameter sensing device is configured to communicate with the reading device via short range wireless communication.

8. The system of claim 1, wherein the parameter sensing device includes a sensing patch, the sensing patch includes:
- a sensing circuit including a sensor unit operable to detect one or more physiological parameters, the sensing circuit configured to process signals obtained by the sensor unit and communicate with the reading device via wireless communication link;
- an antenna configured to receive from, and transmit to, the reading device a radio frequency signal; and
- a substrate supporting the sensing circuit and the antenna and configured to be removably attached to a body surface of the subject.

9. The system of claim 1, wherein:
- the physiological parameter is a temperature; and
- the parameter sensing device is configured to detect the temperature at a body surface of the subject on which the parameter sensing device is attached.

10. A method of obtaining a physiological parameter of a subject, the method comprising:
- obtaining a first physiological parameter at a first time using a parameter sensing device, the parameter sensing device attached to a body of the subject;
- obtaining a second physiological parameter at a second time using the parameter sensing device, the second time being later than the first time;
- calculating a parameter difference between the first physiological parameter and the second physiological parameter;
- comparing the parameter difference with a threshold;
- if the parameter difference is less than the threshold, storing a stability indication flag in the parameter sensing device, the stability indication flag adapted for indicating that physiological parameter has stabilized over time; and
- if the parameter difference is less than the threshold, outputting the second physiological parameter as a detected parameter.

11. The method of claim 10, further comprising:
- if the parameter difference is not less than the threshold, predicting a stabilized parameter before the physiological parameter is stabilized over time; and
- outputting the stabilized parameter as a detected parameter.

12. The method of claim 10, wherein the parameter sensing device is maintained to be activated for a first period of time.

13. The method of claim 12, further comprising:
- transmitting a second trigger signal to the parameter sensing device to activate the parameter sensing device;
- determining that the stability indication flag is stored in the parameter sensing device; and
- obtaining a third parameter shortly after the parameter sensing device is activated.

14. The method of claim 13, wherein the third parameter is obtained within a second period of time after the parameter sensing device is activated by the second trigger signal, the second period of time being shorter than the first period of time.

15. The method of claim 10, wherein:
- the physiological parameter is a temperature; and
- the parameter sensing device is configured to detect the temperature at a body surface of the subject on which the parameter sensing device is attached.

16. The method of claim 10, further comprising:
- prior to obtaining a first physiological parameter, transmitting a trigger signal to a parameter sensing device to activate the parameter sensing device.

17. The method of claim 10, further comprising:
- after storing a stability indication flag in the parameter sensing device, extending reading intervals at which a physiological parameter is obtained.

18. An apparatus for communicating with a temperature sensing device and obtaining a temperature of a subject from the temperature sensing device, the apparatus comprising:
- a processing device configured to control operation of the apparatus;
- a display screen; and
- a computer readable data storage device storing software instructions that, when executed by the processing device, cause the apparatus to:
  - transmit a trigger signal to the temperature sensing device to activate the temperature sensing device, the temperature sensing device attached to a body of the subject;
  - obtain a first temperature at a first time using the temperature sensing device;
  - obtain a second temperature at a second time using the temperature sensing device, the second time being later than the first time;
  - calculate a temperature difference between the first temperature and the second temperature;
  - compare the temperature difference with a threshold;
  - if the temperature difference is less than the threshold, store a stability indication flag in the temperature sensing device, the stability indication flag adapted for indicating that the temperature has stabilized over time;
  - if the temperature difference is less than the threshold, output the second temperature as a detected parameter;
  - if the temperature difference is not less than the threshold, predict a stabilized temperature before the temperature is stabilized over time;
  - display the stabilized temperature as a detected temperature on the display screen; and
  - deactivate the temperature sensing device.

* * * * *